United States Patent [19]
Schmid et al.

[11] Patent Number: 5,591,845
[45] Date of Patent: Jan. 7, 1997

[54] PROCESS FOR THE PRODUCTION OF SURFACTANTS HAVING IMPROVED DETERGENCY

[75] Inventors: Karl Schmid, Mettmann; Brigitte Giesen; Andreas Syldath, both of Duesseldorf, all of Germany

[73] Assignee: Henkel Kommanditgesellschaft auf Aktien, Dusseldorf, Germany

[21] Appl. No.: 403,856

[22] PCT Filed: Sep. 16, 1993

[86] PCT No.: PCT/EP93/02508

§ 371 Date: Mar. 22, 1995

§ 102(e) Date: Mar. 22, 1995

[87] PCT Pub. No.: WO94/07901

PCT Pub. Date: Apr. 14, 1994

[30] Foreign Application Priority Data

Sep. 25, 1992 [DE] Germany ............. 42 32 165.4

[51] Int. Cl.$^6$ ............. C07H 15/00; C07H 15/04; C08B 37/00
[52] U.S. Cl. ............. 536/124; 536/18.6; 536/123.1; 536/126; 424/49; 424/65; 424/70.13; 424/70.19; 510/405; 510/473
[58] Field of Search ............. 536/18.6, 123.1, 536/124, 126; 252/174.17, DIG. 5, DIG. 13, DIG. 14; 424/49, 65, 70.13, 70.19

[56] References Cited

U.S. PATENT DOCUMENTS 4,889,925  12/1989  Schmid et al. ............. 536/18.6
5,266,690  11/1993  McCurry, Jr. et al. ............. 536/18.6
5,431,840   7/1995  Soldanski et al. ............. 252/174.17
5,449,763   9/1995  Wulff et al. ............. 536/18.6

FOREIGN PATENT DOCUMENTS 0231890  8/1987  European Pat. Off. .
0301298  2/1989  European Pat. Off. .
4117689  3/1992  Germany .
9003216  4/1990  WIPO .
9003977  4/1990  WIPO .

OTHER PUBLICATIONS

Fette, Seifen, Anstrichm., 74, 163 (1972).

Primary Examiner—John Kight
Assistant Examiner—Howard C. Lee
Attorney, Agent, or Firm—Wayne C. Jaeschke; John E. Drach; Henry E. Millson, Jr.

[57] ABSTRACT

A process for the production of surface-active compounds having improved detergency comprising hydrolyzing a water-containing paste of an alkyl or alkenyl oligoglycoside of the formula (I):

$$R^1O(G)_p \qquad (I)$$

wherein $R^1$ is an alkyl or alkenyl radical having from about 4 to about 22 carbon atoms, G is a sugar unit having 5 or 6 carbon atoms and p is a number of 1 to 10 for a period of from about 5 minutes to about 10 days at a temperature of from about 70° to about 180° C. and under pressures of from about 1 to about 50 bar.

19 Claims, No Drawings

PROCESS FOR THE PRODUCTION OF SURFACTANTS HAVING IMPROVED DETERGENCY

BACKGROUND OF THE INVENTION

This invention relates to a process for the production of surface-active compounds having improved detergency, in which water-containing pastes of alkyl and/or alkenyl oligoglycosides are subjected to hydrolysis at elevated temperature and optionally under pressure.

STATEMENT OF RELATED ART

Alkyl oligoglycosides, more particularly alkyl oligoglucosides, are nonionic surfactants which are acquiring increasing significance by virtue of their excellent detergent properties and their high ecotoxicological compatibility. They are normally produced from native raw materials, such as for example fatty alcohol and sugar or starch sirup, which are acetalized in the presence of acidic catalysts.

Although the synthesis of alkyl oligoglucosides has been optimized for some considerable time and is now among the industrial processes, it still happens that two batches which have been produced under the same conditions show significance differences in detergency.

In this connection, it was proposed in DE-A1 41 17 689 (Henkel) to add small quantities of anionic surfactants to water-containing alkyl oligoglucosides to improve their performance. However, this involves an additional process step which is undesirable.

Accordingly, the problem addressed by the present invention was to provide a process which would guarantee the production of alkyl and/or alkenyl oligoglycosides of consistently high detergent performance.

DESCRIPTION OF THE INVENTION

The present invention relates to a process for the production of surface-active compounds having improved detergency, in which water-containing pastes of alkyl and/or alkenyl oligoglycosides corresponding to formula (I):

$$R^1O\text{-}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10, are subjected to hydrolysis for 5 mins. to 10 d at temperatures of 70° to 180° C. and under pressures of 1 to 50 bar.

It has surprisingly been found that the subsequent heat treatment of water-containing alkyl and/or alkenyl oligoglycoside pastes guarantees an improvement in the detergent performance of batches of otherwise unsatisfactory quality. The invention is based on the observation that heating of the water-containing pastes results in the hydrolysis or liquefaction of relatively high molecular weight units optionally containing water of crystallization with minimal washing activity, which has an advantageous effect on the detergent properties of the products. In addition, the sugar component can undergo partial oxidation, albeit to a lesser extent, to form anionic surfactants which also contribute towards the effect described above.

Alkyl and/or alkenyl oligoglycosides

Alkyl and alkenyl oligoglycosides are known substances which may be obtained by the relevant methods of preparative organic chemistry. EP-A1-0 301 298 and WO 90/03 977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 1.3), which are obtained as first runnings in the separation of technical $C_{8\text{-}18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol having a DP of 1 to 3 are preferred.

Since the presence of water is essential for hydrolysis, water-containing pastes of the alkyl and/or alkenyl oligoglucosides are normally used as the starting material. It does not matter whether finished preparations are subjected to subsequent heat treatment or whether water is added to substantially water-free products immediately after their production and the products are subsequently hydrolyzed. It is of advantage to use water-containing pastes which have a solids content of 10 to 99% by weight, preferably 30 to 70% by weight and more preferably 50 to 60% by weight, based on the paste.

So far as the hydrolysis is concerned, it is important to bear in mind that the parameters water content, temperature, pressure and residence time are interrelated. For example, products of the consistently high quality required can be obtained both with short residence times at high temperature and with long residence times at low temperatures. With increasing water content, either the temperature or the residence time may be reduced. Finally, it is possible by applying pressure to reduce at least one of the three other parameters and, in particular, to adjust short residence times. Accordingly, this embodiment is preferred for economic reasons.

Where the hydrolysis is carried out in the absence of pressure, it has proved to be optimal to use pastes with a solids content of 10 to 20% by weight (i.e. with a water content of 80 to 90% by weight) and to heat them for 1 to 10 d to 70° to 90° C. This can be done, for example, in a stirred tank reactor, an inert gas blanket counteracting oxidative damage to and unwanted discoloration of the product.

Hydrolysis under pressure may be carried out discontinuously in an autoclave, although it is preferably carried out continuously, for example in a pressure hydrolysis coil. It has proved to be optimal to hydrolyze pastes with a solids content of 70 to 90% by weight (water content 10 to 30% by weight) at 70° to 150° C. and preferably at 90° to 130° C., the residence time being from 5 to 120 minutes and preferably from 15 to 60 minutes. The hydrolysis is normally carried out under autogenous pressure, i.e. under pressures of 2 to 25 bar and preferably 5 to 10 bar.

Commercial Applications

The alkyl and/or alkenyl oligoglycosides obtainable by the process according to the invention are distinguished by consistently good detergent properties. Accordingly, they are suitable for the production of laundry detergents, dishwashing detergents and cleaning products and also hair-care and personal hygiene products in which they may be present in quantities of 1 to 50% by weight and preferably 10 to 30% by weight, based on the particular product.

The following Examples are intended to illustrate the invention without limiting it in any way.

EXAMPLES

I. Substances used

A) Plantaren ® APG 600 (a product of Henkel KGaA, Düusseldorf/FRG) $C_{12/14}$ cocoalkyl oligoglucoside
Solids content: 50% by weight
Average degree of polymerization: 1.3

B) Plantaren ® APG 600 (a product of Henkel KGaA, Düsseldorf/FRG) $C_{12/14}$ cocoalkyl oligoglucoside, freeze-dried
Solids content: 96% by weight
Average degree of polymerization: 1.3

II. Test conditions

The so-called "saucer test" [Fette, Seifen, Anstrichm., 74, 163 (1972)] was carried out to demonstrate detergent performance. The test was carried out with water at 50° C./16° d, with 0.075 g of cocoalkyl oligoglucoside (in the form of a 2.5% by weight stock solution) per liter of water (pH= 7–7.5) and with beef tallow soil (BfTa). The tallow soil was used in a quantity of 2 g per saucer (saucer approx. 14 cm in diameter, soil distributed in the depression). The soiled saucers were washed under the described conditions after standing for 24 h at room temperature.

III. Heat treatment

50% by weight pastes of a cocoalkyl oligoglucoside (A1 to A9) were heated for 5 mins. to 10 d at temperatures of 70° to 180° C. in a drying cabinet (Examples 1 to 3) or under autogenous pressure in an autoclave (Examples 4 to 10). Their cleaning performance was then determined by the saucer test. The cleaning performance of the pastes before storage was equivalent to 8 saucers. The results are set out in Table 1.

TABLE 1

Cleaning performance in the saucer test after heat treatment

| Example | T °C. | A1 | A2 | A3 | A4 | A5 | A6 | A7 | A8 | A9 |
|---|---|---|---|---|---|---|---|---|---|---|
| 1 | 70 | | | | | | | 8 | 8 | 9 |
| 2 | 80 | | | | | | 8 | 8 | 9 | 10 |
| 3 | 90 | | | | | 8 | 9 | 9 | 9 | 10 |
| 4 | 100 | 8 | 8 | 9 | | 9 | 9 | 10 | | |
| 5 | 120 | 10 | 10 | 10 | 10 | 11 | 11 | | | |
| 6 | 130 | 10 | 10 | 10 | 11 | 11 | | | | |
| 7 | 140 | 11 | 11 | 11 | | | | | | |
| 8 | 150 | 11 | 11 | | | | | | | |
| 9 | 160 | 11 | 11 | | | | | | | |
| 10 | 180 | 11 | | | | | | | | |

Storage times:
A1 = 5 mins.
A2 = 15 mins.
A3 = 30 mins.
A4 = 1 h
A5 = 3 h
A6 = 5 h
A7 = 24 h
A8 = 3 d
A9 = 10 d IV. Pressure hydrolysis A freeze-dried cocoalkyl oligoglucoside (B) was diluted with water having a hardness of 0° d to a paste concentration of 50% by weight and subsequently hydrolyzed at 150° to 180° C. in a continuous pressure hydrolysis coil (residence time 15 to 120 mins., pressure 10 bar, pastes B1 to B5). Cleaning performance was then determined by the saucer test. The cleaning performance of the paste before hydrolysis was equivalent to 8 saucers. The results are set out in Table 2.

TABLE 2

Cleaning performance in the saucer test after pressure hydrolysis
Percentages as % by weight

| Example | WC % | T °C. | B1 | B2 | B3 | B4 | B5 |
|---|---|---|---|---|---|---|---|
| 11 | 4.3 | 150 | 8 | | | 10 | 10 |
| 12 | 7.0 | 150 | | | | 10 | 10 |
| 13 | 10.0 | 150 | | | 8 | 10 | 10 |
| 14 | 10.0 | 180 | | | 8 | | |
| 15 | 20.0 | 150 | 10 | 11 | 11 | 11 | 11 |
| 16 | 50.0 | 150 | | | | | 11 |

Residence times:
B1 = 15 mins.
B2 = 30 mins.
B3 = 45 mins.
B4 = 60 mins.
B5 = 120 mins.

What is claimed is:

1. A process for the production of surface-active compounds having improved detergency comprising hydrolyzing a water-containing paste of an alkyl or alkenyl oligoglycoside of the formula (I):

$$R^1O(G)_p \qquad (I)$$

wherein $R^1$ is an alkyl or alkenyl radical having from about 4 to about 22 carbon atoms, G is a sugar unit having 5 or 6 carbon atoms and p is a number of 1 to 10 for a period of from about 5 minutes to about 10 days at a temperature of from about 70° to about 180° C. and under pressures of from about 1 to about 50 bar.

2. The process of claim 1 wherein $R^1$ is a $C_{4-11}$ alkyl radical, G is a glucose unit and p is a number from 1 to 3.

3. The process of claim 1 wherein $R^1$ is a $C_{12-18}$ alkyl radical, G is a glucose unit and p is a number from 1 to 3.

4. The process of claim 1 wherein the solids content of said water-containing paste is from about 10 to about 99% by weight of said paste.

5. The process of claim 1 wherein said pressure is from about 2 to about 25 bar.

6. The process of claim 1 wherein said process is carried out in a continuous pressure hydrolysis coil.

7. The process of claim 1 wherein in the oligoglycoside of formula I, p is a number of from about 1.2 to about 1.7.

8. The process of claim 7 wherein p is a number from about 1.2 to about 1.4.

9. The process of claim 2 wherein $R^1$ is a $C_{8-10}$ alkyl radical.

10. The process of claim 1 wherein in the oligoglycoside of formula I, $R^1$ is a $C_{12-22}$ primary alkyl group.

11. The process of claim 10 wherein $R^1$ is a $C_{12-14}$ primary alkyl group.

12. The process of claim 11 wherein $R^1$ is derived from a hydrogenated $C_{12/14}$ coconut oil fatty alcohol, and p is a number of from about 1 to about 3.

13. The process of claim 4 wherein the solids content of the paste is from about 30 to about 70% by weight.

14. The process of claim 13 wherein said solids content is from about 50 to about 60% by weight.

15. The process of claim 1 wherein the hydrolysis is carried out in the absence of pressure with the paste having a solids content of from about 10 to about 20% by weight for a period of from about 1 to about 10 days at a temperature of from about 70° to about 90° C.

16. The process of claim 15 wherein the process is carried out using an inert gas blanket.

17. The process of claim 1 wherein the process is carried out under a pressure of from about 2 to about 25 bar with the paste having a solids content of from about 70 to about 90% by weight for from about 5 to about 120 minutes at a temperature of from about 70° to about 150° C.

18. The process of claim 17 wherein the time is from about 15 to about 60 minutes, the temperature is from about 90° to about 130° C., and the pressure is from about 5 to about 10 bar.

19. The process of claim 17 wherein the process is carried out in a continuous pressure hydrolysis coil.

* * * * *